United States Patent
Kang et al.

(10) Patent No.: US 7,304,154 B2
(45) Date of Patent: Dec. 4, 2007

(54) METHOD FOR PRODUCING 2-DEOXY-L-RIBOSE

(75) Inventors: Jae-Sung Kang, Yogin (KR); Mi-Hong Yun, Daejeon (KR); Sang-Dae Lee, Daejeon (KR); Byoung-Chan Jeon, Daejeon (KR); Jeong-Ah Shin, Daejeon (KR)

(73) Assignee: Samchully Pharm. Co., Ltd., Seoul (KR)

( * ) Notice: Subject to any disclaimer, the term of this patent is extended or adjusted under 35 U.S.C. 154(b) by 521 days.

(21) Appl. No.: 10/521,022

(22) PCT Filed: Jul. 15, 2003

(86) PCT No.: PCT/KR03/01398

§ 371 (c)(1),
(2), (4) Date: Jan. 12, 2005

(87) PCT Pub. No.: WO2004/007513

PCT Pub. Date: Jan. 22, 2004

(65) Prior Publication Data

US 2005/0176950 A1      Aug. 11, 2005

(30) Foreign Application Priority Data

Jul. 15, 2002 (KR) .................. 10-2002-0041378

(51) Int. Cl.
*C07H 3/08* (2006.01)
*C07H 3/02* (2006.01)

(52) U.S. Cl. ...................................... 536/124
(58) Field of Classification Search ................. 536/124
See application file for complete search history.

(56) References Cited

OTHER PUBLICATIONS

Chinese Patent Office Action for corresponding Chinese Patent Application No. 038166062 dated Mar. 10, 2006.
Michael E. Jung et al., "Efficient Syntheses of L-Ribose and 2-Deoxy L-Ribose From D-Ribose and L-Arabinose", Tetrahedron Letters, vol. 38, No. 24, pp. 4199-4202 (No. PII: S0040-4039(97)00870-8).
Indian Patent Office Action for corresponding Indian Patent Application No. 186/KOLNP/2005 dated Feb. 6, 2006 (In English).

*Primary Examiner*—Shaojia Anna Jiang
*Assistant Examiner*—Ganapathy Krishnan
(74) *Attorney, Agent, or Firm*—Staas & Halsey LLP

(57) ABSTRACT

The present invention relates to an economic synthetic method of 2-deoxy-L-ribose with easy reaction, separation and purification. The present invention consists of four (4) steps including protection, activation of 3- and 4-OH groups, inversion and deprotection steps. In respect to the cost for equipment, reagent and operation, by the present invention, 2-deoxy-L-ribose can be produced more economically because the invention uses 2-deoxy-L-ribose which is abundant in nature and easily synthesized from D-glucose and adopt simple and yielding process.

4 Claims, No Drawings

METHOD FOR PRODUCING 2-DEOXY-L-RIBOSE

TECHNICAL FIELD

The present invention relates to a synthetic method for the compound having compound (1) below, more specifically, to a mass-produceable and cost-effective synthetic method of compound (1) from 2-Deoxy-D-ribose with easy reaction, separation, and purification.

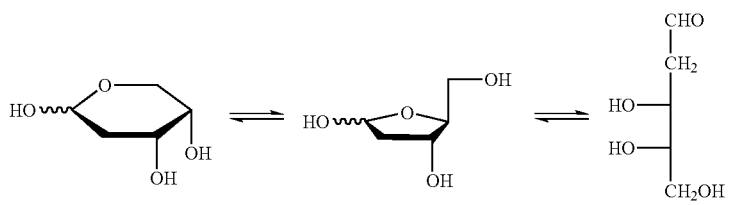

compound (1)

BACKGROUND ART

Recently, natural or modified L-nucleoside are attracting attention as antiviral agents. Some L-nucleosides such as L-thymidine, L-2'-thiacytidine (3TC) and L-2',3'-dideoxycytidine (L-ddC) are much less toxic and have better antiviral activity than their D-isomers. In addition, L-nucleosides have good effect in antisense oligonucleotide therapy.

For the above reasons, many attempts have been made to synthesize L-nucleosides effectively which cannot be obtained as natural products. The efforts has been being focused to economic and mass-produceable preparation method for the derivatives of L-sugar, particularly, 2-deoxy-D-ribose and L-ribose which can be used as key intermediates of L-nucleosides.

Some synthetic methods for 2-deoxy-L-ribose are known from D-ribose, L-arabinose or L-ascorbic acid. (WO 9839347, CS 274394B1, Nucleosides Nucleotidees 1999, 18 (11 & 12), 2357-2365, Tetrahedron: Asymmetry 2000, 11, 1869-176, Org. Lett 1999, 1 (10), 1517-1519).

In these methods, however, expensive or highly toxic reagents are used; difficult separation and purification is required; the overall yield is low; all which are obstacles to the application in the large-scale synthesis.

DISCLOSURE OF INVENTION

Accordingly, the objective of the present invention is to provide a synthetic process of 2-deoxy-L-robse, which allows the cost-effective and large-scale synthesis thanks to the short process, the easy reaction and purification.

BEST MODE FOR CARRYING OUT THE INVENTION

To achieve the above objective, the present invention provides the synthetic process of compound (1) comprising 4 steps; protection, activation and inversion of 3- and 4-OH groups of 2-deoxy-D-ribose, and deprotection.

The present invention provides the synthetic process of compound (1) comprising the steps of; (A) protection step in which aldehyde group of 2-deoxy-D-ribose is protected in the form of acetal. 2-deoxy-1-O-alkyl-D-ribopyranoside is prepared by the reaction of 2-deoxy-D-ribose with alcohol in the presence of acid; (3) activation step in which 3- and 4-OH groups of 2-deoxy-D-ribose are activated. 2-deoxy-1-O-alkyl-3,4-di-(alkanesulfonyl)-D-ribose or 2-deoxy-1-O-alkyl-3,4-di-(arylsulfonyl)-D-ribose is prepared by reaction of the above 2-deoxy-1-O-alkyl-D-ribose with organic sulfonylhalide for activation of 3- and 4-OH; (C) inversion step in which stereochemistry of 3- and 4-OH groups is changed. Reaction of the above 2-deoxy-1-O-alkyl-3,4-di-(alkanesulfonyl)-D-ribose or 2-deoxy-1-O-alkyl-3,4-di-(arylsulfonyl)-D-ribose with a metal salt of organic acid leads to 2-deoxy-L-ribose derivatives of which stereochemistry of 3- and 4-OH is different from the corresponding 2-deoxy-D-ribose derivatives; (D) deprotection step in which 2-deoxy-L-ribose is prepared by consecutive reactions of the step (C) products with acid and base.

Each step will be explained in the following.

(1) Protection

In this step, protecting group is introduced in the form of acetal by the reaction of compound (2), 2-deoxy-D-ribose with alcohol in the presence of acid.

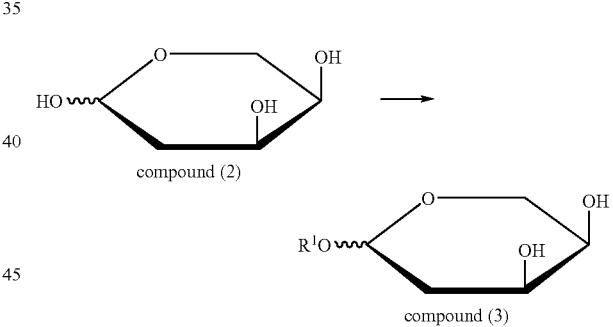

Here, R1 represents a lower alkyl having 1-5 of carbon number, a benzyl or a substituted benzyl. The acid used in this step contains inorganic acid such as hydrochloric acid and sulfuric acid or organic acid such as methanesulfonic acid and p-toluenesulfonic acid and the concentration of acid is preferably 1~10%. A lower alcohol such as methyl alcohol, ethyl alcohol, propyl alcohol and butyl alcohol, benzyl alcohol or substituted benzyl alcohol may be used.

(2) Activation of 3- and 4-OH Groups: Preparation of 2-Deoxy-1-O-alkyl-3,4-di-(alkanesulfonyl)-D-ribose or 2-deoxy-1-O-alkyl-3,4-di-(arylsulfonyl)-D-ribose In this step, compound (4), 2-deoxy-1-O-alkyl-3,4-dialaanesulfonyl)-D-ribose or 2-deoxy-1-O-alkyl-3,4-di-(arylsulfonyl)-D-ribose is obtained by converting 3- and 4-OH groups of compound (3) into 3- and 4-sulfonyl groups by the action of organic sulfonyl halide and an organic base. The purpose of this reaction is the activation of 3- and 4-OH groups for further reaction.

An organic sulfonyl halide used in this step may include a lower alkanesulfonyl halide such as methanesulfonyl chloride and trifluoromethylsulfonyl chloride and arylsulfonyl halide such as bezenesulfonyl chloride and p-toluenesulfonylchloride. Detailed reaction condition is accordance with basic methods of organic synthesis.

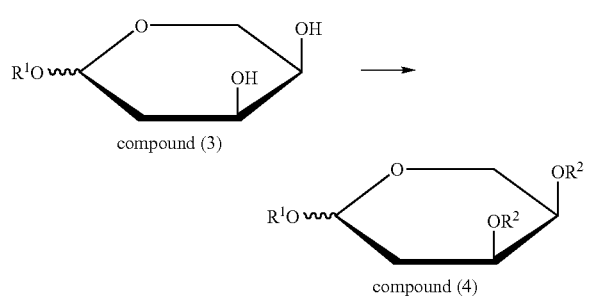

compound (3)

compound (4)

Here, R1 represents a lower alkyl having 1-8 of carbon number, a substituted or unsubstituted benzyl and R2 represents a lower alkylsulfonyl having 1-8 of carbon number, a substituted or unsubstituted aryl sulfonyl group.

(3) Inversion (Conversion to L-sugar from D-sugar): Preparation of the Mixture of 2-deoxy-1-O-alkyl-3-acyl-L-ribose and 2-deoxy-1-O-alkyl-4-acyl-L-ribose Compound (5), the mixture of 2-deoxy-1-O-alkyl-3-acyl-L-ribose and 2-deoxy-1-O-alkyl-4-benzoyl-L-robose in which the stereochemistry of 3- and 4 carbon is changed is prepared through the reaction of compound (4) with a metal salt of organic acid.

A metal salt of organic acid used in this step may include a metal salt of lower alkyl organic acid such as sodium acetate, potassium acetate or a metal salt of aryl organic acid such as sodium benzoate or potassium benzoate. A solvent used in this step may include water and organic solvent such as dimethylformamide (DMF), dimethylacetaride (DMAC), and alohols, but DMF or the mixture of water and organic solvent is preferable in view of solubility of the reactants.

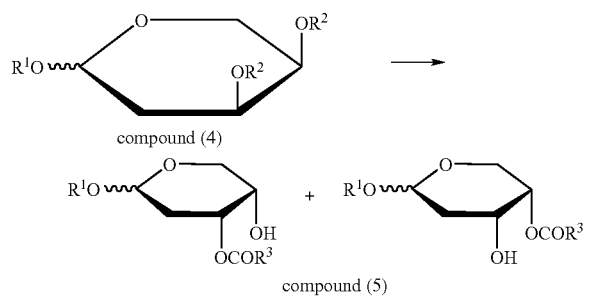

compound (4)

compound (5)

Here, R1 represents a lower alkyl having 1-8 of carbon number, a substituted or unsubstituted benzyl and R2 represents a lower alkylsulfonyl having 1-8 of carbon number, a substituted or unsubstituted aryl sulfonyl group.

(4) Deprotection

Compound (1), 2-deoxy-L-ribose is obtained by the stepwise reactions of compound (5) with acid and base. Acid and base used in deprotection conventionally may also be used in this step. The order of the stepwise reactions may be changed according to its convenience.

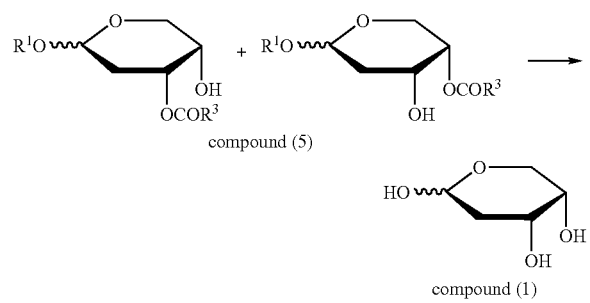

compound (5)

compound (1)

Compound (1) can be used as a raw material for the further reaction without purification or can be purified by the formation of anilide derivative well known as a purification method of 2-deoxy-D-ribose to obtain as solid.

The above preparation method is depicted in the following scheme:

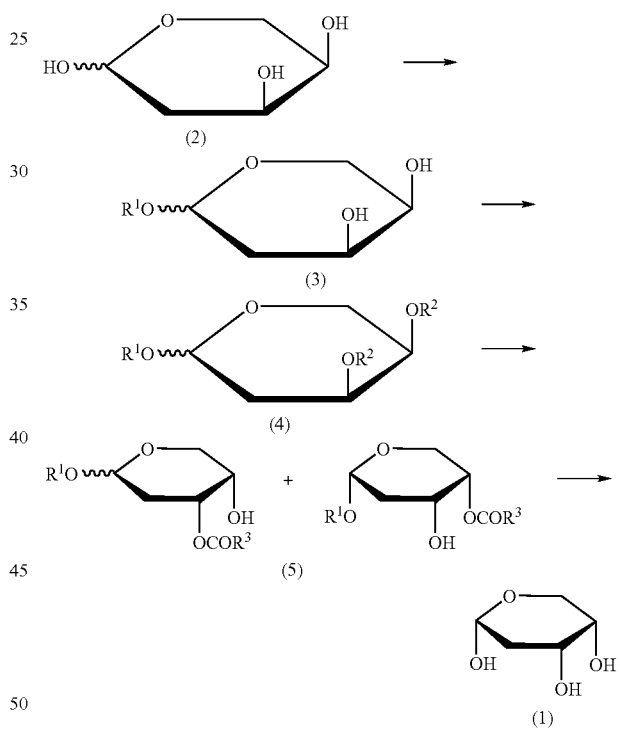

[R1: lower alkyl having 1-8 of carbon number or substituted or unsubstituted benzyl R2: lower alkylsulfonyl having 1-8 of carbon number or substituted or unsubstituted arylsulfonyl R3: lower alkyl having 1-8 of carbon number or substituted or unsubstituted benzyl]

The syntheses described above provide simple preparation method of compound (1) utilizing chief and commercially available reagents without toxic reagent such as heavy metal and easily attainable temperature and pressure range.

In addition, separation and purification is easy without special equipment because the key intermediate and final product can be purified by recrystallization.

The raw material, 2-deoxy-D-ribose is not only abundant in natural products, but also obtained by chemical synthesis. All the above reason make the procedure mass-producible effectively.

To assist in understanding the present invention more clearly, the following embodiments are appended. The embodiments should not, of course, be construed to limit or alter the scope of the present invention. Further, the variations or modifications of the present invention which do not depart from the spirit of the present invention can easily be made by one of ordinary skill in the art and are considered to fall within the scope of the present invention.

PREFERRED EMBODIMENTS

Embodiment 1

Protection: Preparation of 2-deoxy-1-O-butyl-D-ribose

To a cooled butyl alcohol containing 3% HCl (56.4 mL) was added 2-deoxy-D-robse (10 g) and stirred under −2° C. for 16 hours. The reaction mixture was neutralized with triethylamine keeping the temperature under 10° C. and stirred at 20~25° C. The mixture was filtered and washed with acetone (20 mL). The combined filterate and washing solution was concentrated and used for further reaction without purification.

Embodiment 2

Activation of 3- and 4-OH Groups: Preparation of 2-Deoxy-1-O-butyl-3,4-di-(p-toluenesulfonyl)-D-ribose To the solid of 2-deoxy-1-O-butyl-D-ribose obtained in Embodiment 1 were added pyridine (36 mL), p-toluenesulfonyl chloride (42.6 g) stepwise under 30° C. and the mixture was stirred at 27~30° C. for 20 hours. The reaction mixture was heated to 75±2° C. and stirred for 2 hours. After the completion of reaction, the mixture was cooled to 15~20° C. and purified water (30 mL) was added and the resulting mixture was extracted twice with ethyl acetate (30 mL). The extract was concentrated and ethyl alcohol and isopropyl alcohol were added. The solution was cooled, filtered, and dried, to obtain the solid of 2-deoxy-1-O-butyl-3,4-di-(p-toluenesulfonyl)-D-ribose (23 g).

Embodiment 3

Conversion to Inform Sugar from D-Form Sugar: Preparation of 2-deoxy-1-O-butyl-3-benzoyl-L-ribose and 2-deoxy-1-O-butyl-4-benzoyl-L-ribose To the compound obtained in Embodiment 2 (20 g) were added n-butanol (7 mL), water (4.4 mL), N,N-dimethylformamide (27.6 mL) and potassium benzoate (21.2 g) and the mixture was heated to 115° C. and reacted for 8 hours. After the concentration of the reaction mixture, water and ethyl acetate were added to separate organic and water layers. After the organic layer was concentrated, the residue was mixed with water and evaporated again to concentrate N,N-dimethylformamide efficiently. The residue was used for the next reaction.

Embodiment 4

Deprotection: Preparation of 2-deoxy-L-ribose

To the residue obtained in Embodiment 3 were added water (10 mL) and 40% sodium hydroxide solution (10 mL) and the mixture was stirred for 3 hours at room temperature. 6N hydrochloric acid (50 mL) was added to the reaction mixture and the resulting mixture was stirred for 4 hours at 25~30° C. to give 2-deoxy-L-ribose. Through the formation of anilide derivative which was already known for its enatiomer 2-deoxy-D-ribose, pure 2-deoxy-L-ribose was obtained as solid (3.4 g).

INDUSTRIAL APPLICABILITY

The present invention is related to the synthetic method for 2-deoxy-L-ribose in which reaction and purification is easy at easily attainable range of temperature and pressure, and of which reagents are more cheap and less toxic. Additionally, this invention provides more economic method than the previously known process in terms of the costs for equipments, law-materials, and processing by using the low-cost and non-toxic reagents starting from 2-deoxy-D-ribose which is naturally abundant as well as can be synthesized from D-glucose easily.

What is claimed is:

1. A method for producing 2-deoxy-L-ribose comprising the steps of (A) protection step for preparation of 2-deoxy-1-O-alkyl-D-ribopyranoside, of which the aldehyde group in 2-deoxy-D-ribose is protected in the form of acetal, by reacting 2-deoxy-D-ribose with an alcohol in the presence of an acid; (B) activation step for preparation of 2-deoxy-1-O-alkyl-3,4-di-(alkanesulfonyl)-D-ribose or 2-deoxy-1-O-alkyl-3,4-di-(arylsulfonyl)-D-ribose, of which the 3- and 4-OH groups in 2-deoxy-D-ribose are activated, by reacting the above 2-deoxy-1-O-alkyl-D-ribose and an organic sulfonyl halide in the presence of a base; (C) inversion step for preparation of a mixture of 2-deoxy-1-O-alkyl-3-acyl-L-ribose and 2-deoxy-1-O-alkyl-4-acyl-L-ribose, in which the stereochemistry of 3-OH and 4-OH groups are inverted, by reacting the above 2-deoxy-1-O-alkyl-3,4-di-(alkanesulfonyl)-D-ribose or 2-deoxy-1-O-alkyl-3,4-di-(arylsulfonyl)-D-ribose with a metal salt of organic acid; and (D) deprotection step for preparation for 2-deoxy-L-ribose by reactions of the above mixture of 2-deoxy-1-O-alkyl-3-acyl-L-ribose and 2-deoxy-1-O-alkyl-4-acyl-L-ribose with an acid and then with a base, or with a base and then with an acid.

2. The method for producing 2-deoxy-L-ribose according to claim 1, wherein the alcohol used in said protection step is a lower aliphatic alcohol having 1-4 of carbon number or benzyl alcohol.

3. The method for producing 2-deoxy-L-ribose according to claim 1, wherein the organic sulfonyl halide used in said activation step is a lower alkanesulfonyl halide selected from the group consisting of methane sulfonyl chloride and trifluoro methane sulfonyl chloride, or an arylsulfonyl halide selected from the group consisting of benzenesulfonyl chloride and p-toluenesulfonyl chloride.

4. The method for producing 2-deoxy-L-ribose according to claim 1, wherein the metal salt of organic acid used in said conversion step is a metal salt of lower alkyl organic acid having 1-8 of carbon number or a metal salt of aryl organic acid.

* * * * *